United States Patent [19]

Friedrich et al.

[11] Patent Number: 5,817,853
[45] Date of Patent: Oct. 6, 1998

[54] PREPARATION OF ACYLOXYALKOXYSILANES

[76] Inventors: Holger Friedrich, Roxheimer Str. 66, 67240 Bobenheim-Roxheim; Bernd Leutner, Taunusstr. 17, 67227 Frankenthal; Norbert Mronga, Ringstr. 2, 69221 Dossenheim; Raimund Schmid, Im Falkenhorst 1, 67435 Neustadt, all of Germany

[21] Appl. No.: 909,941

[22] Filed: Aug. 12, 1997

[30] Foreign Application Priority Data

Aug. 12, 1996 [DE] Germany .................. 196 32 483.1

[51] Int. Cl.⁶ .................. C07F 7/08; C07F 7/12
[52] U.S. Cl. .................. 556/442
[58] Field of Search .................. 556/442

[56] References Cited

U.S. PATENT DOCUMENTS

| | | | |
|---|---|---|---|
| 3,296,161 | 1/1967 | Kulpa | 260/18 |
| 3,296,195 | 1/1967 | Goossens | 260/46.5 |
| 5,208,359 | 5/1993 | Seiler et al. | 556/442 |
| 5,241,096 | 8/1993 | Kinami et al. | 556/442 |
| 5,387,706 | 2/1995 | Rasmussen et al. | 556/442 |

FOREIGN PATENT DOCUMENTS 465 723   12/1990   European Pat. Off. .

Primary Examiner—Paul F. Shaver

[57] ABSTRACT

A process for preparing a silane of the formula I $$R^1{}_n SiR^2{}_m \qquad (I)$$

where
$R^1$ is —O—Y, n is an integer from 1 to 3, $R^2$ is $$-O-\overset{\overset{\displaystyle O}{\|}}{C}-Z,$$

m is an integer from 1 to 3 and n+m=4, and Y and Z are each, independently of one another, unsubstituted or mono- or polyhalo-substituted $C_1$—$C_{20}$-alkyl, $C_2$—$C_{20}$-alkenyl, $C_2$—$C_{20}$-alkynyl and —$(CH_2)_p$—A, where p is an integer from 0 to 6 and A, which is unsubstituted or substituted by one or more $C_1$–$C_6$-alkyls, is a 3- to 20-membered hydrocarbon ring entails reacting a halosilicon compound of the formula II $$SiX_4 \qquad (II)$$

where
X is fluorine, chlorine, bromine and iodine, with compounds of the formula III and IV, or with an anhydride of the formula V and the compound of the formula IV $$MR^2 \qquad (III)$$

$$H-R^1 \qquad (IV)$$

$$\overset{\overset{\displaystyle O}{\|}}{Z-C}-O-\overset{\overset{\displaystyle O}{\|}}{C-Z} \qquad (V)$$

where $R^1$ and $R^2$, and Z have the above meanings, M is a metal of main group one and two.

19 Claims, No Drawings

PREPARATION OF ACYLOXYALKOXYSILANES

The invention relates to a process for preparing a silane of the formula I $$R^1{}_n SiR^2{}_m \quad (I)$$

where
$R^1$ is —O—Y,
n is an integer from 1 to 3,
$R^2$ is $$-O-\overset{\overset{\displaystyle O}{\|}}{C}-Z,$$

m is an integer from 1 to 3 and n+m=4, and
Y and Z are each, independently of one another, unsubstituted or mono- or polyhalo-substituted $C_1$—$C_{20}$-alkyl, $C_2$—$C_{20}$-alkenyl, $C_2$-$C_{20}$-alkynyl and —$(CH_2)_p$—A, where p is an integer from 0 to 6 and A, which is unsubstituted or substituted by one or more $C_1$–$C_6$-alkyls, is a 3- to 20-membered hydrocarbon ring.

The process comprises reacting a halosilicon compound of the formula II $$SiX_4 \quad (II)$$

where
X is fluorine, chlorine, bromine and iodine, with compounds of the formula III and IV, or with an anhydride of the formula V and the compound of the formula IV $$MR^2 \quad (III)$$

$$H-R^1 \quad (IV)$$

$$Z-\overset{\overset{\displaystyle O}{\|}}{C}-O-\overset{\overset{\displaystyle O}{\|}}{C}-Z \quad (V)$$

where
$R^1$ and $R^2$, and Z have the above meanings,
M is a metal of main group one and two.

U.S. Pat. No. 3,296,195 discloses a process for preparing alkoxyacetoxysilanes, in particular di-tert-butoxydiacetoxysilane, in which tetraacetoxysilane is prepared in a first step from tetrachlorosilane and acetic anhydride and is reacted in a second step with tert-butanol to give the compound mentioned at the outset. The disadvantage of this process is that it has more than one stage, especially that the tetraacetoxysilane must be isolated before reaction with the appropriate alcohol.

U.S. Pat. No. 3,296,161 likewise discloses a process for preparing dialkoxydiacetoxysilanes, in particular di-tert-butoxydiacetoxysilane, in which the tetraacetoxysilane is prepared in a first step from acetic anhydride and tetrachlorosilane and is reacted in a subsequent step with an appropriate alcohol. The disadvantage of this process is likewise the fact that the tetraacetoxysilane must be isolated before reaction with the alcohol.

EP-B 0 465 723 discloses a process for preparing di-tert-butoxydiacetoxysilane by reacting tetraacetoxysilane and tert-butanol. In this case, because of the use of acetic acid, gaseous HCl is produced and must be removed as far as possible in an elaborate manner because, otherwise, side reactions, for example the formation of polymers, occur to an unwanted large extent.

It is an object of the present invention to overcome the disadvantages detailed above. In particular, it is an object of the invention to provide a process for preparing compounds of the formula I which makes it possible to carry out the reaction as one-pot process without the need to carry out the elaborate synthesis and isolation of precursors, especially of tetraacyloxysilane, before reaction with an alcohol. It is another object of the invention to prepare the compounds of the formula I directly from halosilane, salts and/or anhydride of the appropriate carboxylic acid and alcohol.

We have found that these objects are achieved by a process as defined above.

The substituents Y and Z according to the invention can be, independently of one another, $C_1$—$C_{20}$-alkyl, preferably $C_1$—$C_{12}$-alkyl and particularly preferably $C_1$—$C_6$-alkyl, $C_2$—$C_{20}$-alkenyl, preferably $C_2$—$C_{12}$-alkenyl and particularly preferably $C_2$—$C_6$-alkenyl, and $C_2$—$C_{20}$-alkynyl, preferably $C_2$—$C_{12}$-alkynyl and particularly preferably $C_2$—$C_6$-alkynyl.

Preferred alkyl radicals according to the invention are methyl, ethyl, n-butyl, isobutyl, sec-butyl, tert-butyl, n-pentyl, isopentyl, sec-pentyl, 1,1-dimethylpropyl (tert-pentyl), neopentyl, 1,2-dimethylpropyl, n-hexyl, isohexyl, sec-hexyl, neohexyl, n-heptyl, isoheptyl, neoheptyl, n-octyl, isooctyl, neooctyl, n-nonyl, isononyl, neononyl, n-decyl, isodecyl, neodecyl, n-undecyl, isoundecyl, neoundecyl, n-dodecyl, isododecyl, neododecyl, n-tetradecyl, n-hexadecyl, n-octadecyl and n-eicosyl, with $C_1$—$C_4$-alkyl radicals being particularly preferred, such as methyl, ethyl, n-propyl, isopropyl, n-butyl, isobutyl, sec-butyl and tert-butyl.

Particularly preferred alkenyl radicals according to the invention are n-propenyl, isopropenyl, n-butenyl, isobutenyl, sec-butenyl, tert-butenyl, n-pentenyl, isopentenyl, neopentenyl, 1,2-dimethylpropenyl, n-hexenyl, isohexenyl, sec-hexenyl, neohexenyl, n-heptenyl, isoheptenyl, neoheptenyl, n-octenyl, isooctenyl, neooctenyl, n-nonenyl, isononenyl, neononenyl, n-decenyl, isodecenyl, neodecenyl, n-undecenyl, iso-undecenyl, neoundecenyl, n-dodecenyl, isododecenyl and neododecenyl.

Particularly preferred $C_2$—$C_6$-alkenyl radicals are ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,2-dimethyl-1-propenyl, 1,2-dimethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3- butenyl, 1,3-dimethyl-2-butenyl, 1,3-dimethyl-3-butenyl, 2,2-dimethyl-3-butenyl, 2, 3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl.

Preferred $C_2$—$C_6$-alkynyl radicals according to the invention are ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-hexynyl, 2-methyl-3-pentynyl, 1-methyl-4-pentynyl, 2-methyl-3-pentynyl, 2-methyl-4-pentynyl, 3-methyl-1-pentynyl, 4-methyl-4-pentynyl, 4-methyl-1-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Particularly preferred alkynyl radicals according to the invention are ethynyl, 1propynyl, 2-propynyl, 1-butynyl, 2-butynyl, 3-butynyl, 3-butyn-2-yl, 1-methyl-2-propynyl, 1-pentynyl, 2-pentynyl, 3-pentynyl, 1-hexynyl, 2-hexynyl, 3-hexynyl, 4-hexynyl, 5-hexynyl, 3-hexyn-2-yl, 2-ethynyl-cyclohexyl.

Radicals which are particularly preferred according to the invention are radicals having 6 to 20 carbon atoms which are bonded via a tertiary carbon, to which another alkyl radical is connected via a triple bond. Examples of these radicals which are particularly preferred according to the invention are, especially for use as alcohol of the general formula IV, 1-(1-butynyl)cyclohexanyl, 1-(1-butynyl)cyclopentanyl, 4-phenyl-2-methyl-3-butyn-2-yl, 2-methyl-3-pentyn-2-yl, 3-methyl-4-hexyn-3-yl, 4-methyl-2-octyn-4-yl, 4-methyl-2-heptyn-4-yl, 2-methyl-3-hexyn-2-yl, 3-methyl-4-heptyn-3-yl, 1-propynyl-1-cyclohexanyl, 1 -ethynyl- 1 -cyclohexanyl. A is a 3–20-membered, preferably 3–10- and particularly preferably 3–6-membered hydrocarbon ring. This hydrocarbon ring may consist of one or more rings which can be saturated, partially saturated and unsaturated.

Saturated hydrocarbon rings which are preferred according to the invention are cyclopropyl, cyclobutyl, cyclopentyl, cyclohexyl, cycloheptyl, cyclooctyl, norbornyl and adamantyl, with cyclopentyl, cyclohexyl, cycloheptyl and cyclooctyl being particularly preferred.

The partially saturated hydrocarbon rings according to the invention may have one or more double bonds and/or triple bonds. Examples of cyclic radicals with a double bond are cyclopropenyl, cyclobutenyl, cyclopentenyl, cyclohexenyl and cycloheptenyl. Examples of cyclic radicals with a triple bond are cyclononynyl, cyclodecynyl, cycloundecynyl and cyclododecynyl. An example which may be mentioned of a cyclic radical with a double bond and a triple bond is cyclohexadec-2-en-4-ynyl. Suitable cyclic radicals with two double bonds are cyclobutadienyl and 2,4-cyclohexadienyl.

The hydrocarbon rings according to the invention have 3 to 20, preferably 3 to 10 and particularly preferably 3 to 7, members. Furthermore, the hydrocarbon rings according to the invention may be both unsaturated, partially saturated and saturated. In addition, it may furthermore be preferred according to the invention for the hydrocarbon rings to be substituted by one or more halogens.

Examples of preferred radicals of saturated hydrocarbon rings with 3 to 7 members or 3 to 7 carbon atoms are cyclopropyl, cyclobutyl, cyclopentyl, cyclohexyl and cycloheptyl.

Preferred partially saturated hydrocarbon rings are radicals with one, two or three multiple bonds, ie. double or triple bonds. Examples with a double bond which are preferred according to the invention are cyclopropenyl, cyclobutenyl, cyclopentenyl, cyclohexenyl and cycloheptenyl. Preferred examples with a triple bond are cyclononynyl, cyclodecynyl, cycloundecynyl, cyclododecynyl and cyclotridecynyl. Preferred radicals of hydrocarbon ring systems with two double bonds are cyclobutadienyl, cyclopentadienyl, cyclohexadienyl and cycloheptadienyl.

The unsaturated hydrocarbon rings are preferably aromatic radicals with, preferably, 6 to 18 carbon atoms, such as phenyl, 1-naphthyl, 2-naphthyl, 1-anthryl, 2-anthryl and 9-anthryl, with phenyl, 1-naphthyl and 2-naphthyl being preferred and phenyl being particularly preferred. Alkyl-substituted aryl radicals are 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl with toluyl and xylyl being particularly preferred. The aromatic radicals according to the invention may be halogenated.

Examples of halogenated aryl radicals are aromatic systems which are substituted one or more times by halogens such as fluorine, chlorine, bromine, iodine, preferably fluorine, chlorine and bromine and particularly preferably chlorine, such as 2-, 3-, 4-chlorophenyl, 2,4-dichlorophenyl, 2,6-dichlorophenyl and 2,4,6-trichlorophenyl.

Examples of particularly preferred halogenated alkyl radicals are chloromethyl, dichloromethyl, trichloromethyl, 2-chlorocyclohexyl, 3,4-dichlorocyclohexyl.

Examples of combinations of Y and Z which are preferred according to the invention are (the substituent for Y is mentioned first and the substituent for Z is mentioned second) tert-butyl, methyl; tert-butyl, ethyl; tert-butyl, n-propyl, and tert-amyl, methyl; tert-amyl, ethyl; tert-amyl, propyl.

X represents the halogens fluorine, chlorine, bromine and iodine, preferably fluorine, chlorine and bromine and particularly preferably chlorine and bromine. It is likewise possible to employ mixed tetrahalosilicon compounds. Of all the silicon tetrahalides, tetrafluorosilane and tetrachlorosilane are preferred, and tetrachlorosilane is particularly preferred.

M represents the metals of main groups 1 and 2, in particular the metals of main group 1. Of the metals in main group 1, lithium, sodium and potassium are preferred, and sodium is particularly preferred.

The process according to the invention can preferably take place as a one-pot reaction. A one-pot reaction means a chemical reaction which may take place in several steps but the intermediates thereof are not isolated. In the one-pot reaction it is possible for all the reactants either to be present in the reaction vessel from the outset or to be added successively, and another reactant may be added before completion of the addition of the one previously added.

In the process according to the invention, the compounds of the formula III and IV and/or V can be added to the compound of the formula II preferably simultaneously or successively, and in a preferred embodiment of the process according to the invention it is possible to add first the compound III and then the compound IV and/or V, and in another embodiment it is possible to add first the compound IV and/or V and then the compound III, to the compound II.

It is furthermore preferred in the process according to the invention for it be unnecessary to isolate the intermediates produced in the reaction of the compound of the formula II with the compounds of the formulae III and IV, or in the reaction of the compound of the formula II with an anhydride of the formula V and IV. In particular, it is unnecessary in the process according to the invention to isolate intermediates which result from the reaction of the compound of the formula II with the compound of the formula III or from the reaction of the compound of the formula II with the compound of the formula IV or from the reaction of the compound of the formula II with an anhydride of the formula V.

In a particularly preferred embodiment of the process according to the invention, the compound of the formula II is introduced into a nonpolar or aprotic polar solvent which itself preferably does not react with a halosilane, and the compounds III and IV and/or V are added either undiluted or likewise in a nonpolar or aprotic polar solvent.

Examples of nonpolar solvents according to the invention are petroleum fractions boiling between 40° and 100° C., for example petroleum ether, especially the petroleum ether fraction with the boiling range from 40° to 60° C., and n-pentane, n-hexane, n-heptane, n-octane and n-nonane.

However, particularly preferred aliphatic hydrocarbons are also the mixed isomers of pentane, hexane, heptane, octane, isooctane, nonane and decane, and mixtures thereof. It is likewise also possible to employ cyclo-aliphatic hydrocarbons such as cyclopentane, cyclohexane and methylcyclohexane. It is furthermore possible to use chlorinated hydrocarbons such as chloroform, methylene chloride, dichloroethane and tetrachloromethane as nonpolar solvents. Nonpolar solvents according to the invention are aromatic solvents such as benzene, toluene, xylene and ethylbenzene. Examples of aprotic polar solvents which can be employed in the process according to the invention are ethers such as diethyl ether, methyl tert-butyl ether (MTBE), tetrahydrofuran and 1,2-dimethoxyethane. Other aprotic polar solvents according to the invention are dimethylformamide, N-methylpyrrolidone and dimethyl sulfoxide.

It is also possible to employ mixtures of the abovementioned solvents for the process according to the invention.

It is furthermore possible to increase the solubility of the reactants by adding appropriate aids. Examples of aids of this type are surface-active agents and soaps.

The reactants in the process according to the invention can be present in the abovementioned solvents, for example, in solution, in suspension, in emulsion, in a slurry or as dispersion.

However, it is equally possible for the process according to the invention to be carried out without solvent.

In the process according to the invention, the compound of the formula II is preferably dissolved in one of the abovementioned solvents but, especially when it is a tetrachlorosilane, it is preferably added undiluted to the reaction.

The compounds of the general formula III are, especially in the case of sodium acetate, taken up in one of the abovementioned solvents, but preferably dispersed. Petroleum ether and hexane have proven particularly suitable for dispersing the compound of the formula III, especially sodium acetate. However, it is equally possible to employ the compound of the formula III as solid directly in the reaction.

The alcohol of the formula IV or the anhydride of the formula V can be introduced into the reaction with or without one of the abovementioned solvents. If the alcohol of the formula IV or the anhydride of the formula V is liquid under the reaction conditions, especially at room temperature, it is preferably employed without solvent. If the alcohol or the anhydride is solid under the reaction conditions, especially at room temperature, it is preferably employed as a solution in one of the abovementioned solvents.

The process according to the invention can be carried out continuously or batchwise, and batchwise is preferred.

The process according to the invention is carried out at a temperature in the range from 10° to 100°, preferably 20° to 70° and particularly preferably 40° to 60° C. over a period of from 1 minute to 24 hours, preferably 1 to 3 hours and particularly preferably 1.5 to 2 hours, under reduced, atmospheric or elevated pressure, preferably under atmospheric pressure.

In a preferred embodiment, the compound of the formula III, preferably sodium acetate, is converted into a dispersion in an inert solvent, preferably hexane or petroleum ether (component A). The compound of the formula II, preferably tetrachlorosilane, dissolved in a solvent, but preferably undiluted (component B) and the compound of the formula IV, preferably tert-butanol, dissolved in a solvent, but preferably undiluted (component C), are then combined.

In another embodiment of the present invention, component A is introduced first and components B and C are added simultaneously.

In another embodiment according to the invention, component A is introduced first and addition of component B is started before the addition of component C.

In another embodiment according to the invention, component A is introduced first and the addition of component C is started before the addition of component B. This embodiment is particularly advantageous when higher alcohols are employed.

In another embodiment of the present invention, component B and component C are alternately added in portions to component A, it being possible to start the alternate addition both with component B and with component C, but preferably with component B.

In another embodiment according to the invention, component B is introduced first and component A is added as solid and/or as suspension, after which component C is added.

It is possible by the above preferred embodiments to prepare compounds of the formula I where n and m can be 1 and 3, 2 and 2, and 3 and 1, with 2 for each of m and n being preferred.

It is advantageous in the embodiments of the process according to the invention to pay attention to the molar ratio between component C (or compound III) and component B (or compound IV) depending on the values of n and m.

In the case where the silane of the formula I according to the invention is prepared via an anhydride of the formula V in place of the compound of the formula III, an embodiment which is preferred according to the invention comprises firstly introducing the compound of the formula II, preferably tetrachlorosilane, dissolved in a solvent, but preferably undiluted (component B), and adding the anhydride of the formula V dissolved in an inert solvent, but preferably undiluted (component A'), and the appropriate alcohol of the formula IV dissolved in a solvent, but preferably undiluted (component C).

In another embodiment of the present invention, component A' is introduced first and components B and C are added simultaneously.

In another embodiment according to the invention, component A' is introduced first and addition of component B is started before the addition of component C.

In another embodiment of the present invention, component A' and component C are alternately added in portions to component B, preferably starting the alternate addition with component A'.

It is possible by the above preferred embodiments to prepare compounds of the formula I where n and m can be 1 and 3, 2 and 2, and 3 and 1, with 2 for each of m and n being preferred.

In the case where n is 1 and m is 3, care should be taken that the molar ratio of component C to component B during the reaction is always≦1, it being preferred for the molar ratio at the end of the reaction to be 1. If m and n are each 2, care should be taken that the molar ratio of component C to component B during the reaction is always≦2, with the ratio at the end of the reaction preferably being 2. If n is 3 and m is 1, it is advantageous for the molar ratio of component C to component B during the reaction always to be≦3, with the molar ratio at the end of the reaction preferably being 3. It may furthermore be preferred according to the invention for the molar ratio of A or A' to component B to be≧4:1.

It is furthermore possible for the process according to the invention, preferably the addition of components A or A', B and C, to take place independently of one another at from 10° to 100°, preferably 20° to 70° and particularly preferably 40° to 60° C.

The time for addition of components A or A', B and C can be, independently of one another, from 1 minute to 24 hours, preferably 1 to 3 and particularly preferably 1.5 to 2 hours.

It is advantageous in the embodiments of the process according to the invention to pay attention to the molar ratio between component C (or compound III) and component B (or compound IV) depending on the values of n and m. Also when the anhydride is used, it is advantageous in the embodiments of the process according to the invention to pay attention to the molar ratio between component C (or compound II) and component B (or compound IV) depending on the values of n and m in the manner detailed previously.

It may furthermore be advantageous according to the invention, preferably when the compound of the formula 11 is introduced first and the anhydride of the formula V is added, to remove any acid chloride which is produced, preferably by distillation, and to start adding the alcohol of the formula IV only after starting the removal of the acid chloride, but preferably after completion of the removal of the acid chloride.

Workup of the product of the formula I prepared by the process according to the invention preferably takes place by removing the salt of the formula MX, preferably sodium chloride, by filtration, decantation or similar methods known to the skilled worker. Any solvent which is present, in particular hexane or petroleum ether, and the reaction product of the formula $HR^2$, preferably acetic acid, are removed, for example by distillation, vacuum distillation or chromatography or another process familiar to the skilled worker, and the product is purified, with vacuum distillation with a bottom temperature not exceeding 100° C. being preferred. Distillation may equally take place with a thin film evaporator or by using a distillation column. If an anhydride is employed in the process according to the invention, it is preferable to remove the acid halide produced from the anhydride, preferably by distillation, it being particularly preferred according to the invention to remove the acid halide immediately after its formation. Further workup takes place as detailed above.

The invention is now illustrated by means of the following examples.

EXAMPLES

Example 1
Synthesis of diacetoxydi-tert-butoxysilane 200 ml of hexane were introduced into a four-neck flask with reflux condenser, stirrer, dropping funnel and thermometer, and 82 g (1 mol) of sodium acetate were made into a slurry therein. The slurry was heated to 50° C., and stirred at high speed and 42.5 g (0.25 mol) of tetrachlorosilane were added dropwise through the dropping funnel over the course of 15 minutes, during which the temperature rose to 65° C. owing to the heat of reaction. The reaction mixture was then stirred at 65° to 67° C. for 1 hour and subsequently stirred without further heating for 16 hours, during which the reaction mixture cooled to room temperature. It was then heated to 65° C. again, 37 g (0.5 mol) of tert-butanol were added dropwise over the course of 5 minutes, and subsequently the reaction mixture was stirred at 50° C. for 3 hours.

The reaction mixture at 50° C. was filtered through a pressure filter funnel and the filter cake was washed with 200 ml of n-hexane. The filtrate was then concentrated in a rotary evaporator at 50° C. in vacuo.

62 g (85%) of diacetoxydi-tert-butoxysilane were obtained with a purity of 95 to 96% (according to gas chromatogram). Distillation through a column at 56° C. and 0.1 mbar afforded 57.2 g (78.5%) of diacetoxydi-tert-butoxysilane with a purity of 97 to 98% according to gas chromatography. The $^1$H-NMR spectrum corresponded to the structure of diacetoxydi-tert-butoxysilane.

Example 2
Synthesis of diacetoxydi-tert-butoxysilane 800 ml of hexane were introduced into a four-neck flask with reflux condenser, stirrer, dropping funnel and thermometer, and 345 g (4.2 mol) of sodium acetate were dispersed therein. To this were added dropwise, without previous heating, 170 g (1 mol) of tetrachlorosilane over the course of 30 minutes, during which the temperature of the reaction mixture rose to about 70° C. and the solvent refluxed. The reaction mixture was subsequently stirred at 70° C. for 1 hour and then cooled to 50° C., 148 g (2 mol) of tert-butanol were added over the course of 5 minutes while stirring and the mixture was then stirred at 50° to 60° C. for 1.5 hours and subsequently filtered through a pressure filter funnel. The filter cake was washed three times with 200 ml of n-hexane at 50° C. each time, and the combined filtrates were concentrated using a rotary evaporator at 60° C. under one mbar.

The yield of diacetoxydi-tert-butoxysilane was 276.2 g (94.6%) with a purity, determined by gas chromatography, of more than 98%.

Example 3
Synthesis of diacetoxydialkoxysilanes with acetic anhydride 221 g (1.3 mol) of $SiCl_4$ are introduced into a flask which is equipped with internal thermometer, dropping funnel, stirrer and distillation apparatus and, while stirring, 530 g (5.2 mol) of acetic anhydride and 4 g of acetic acid were added. The mixture is then stirred at 45°–50° C. for 1 h and subsequently 404 g of acetyl chloride are distilled out (at 50°–58° C.). Then 2.6 mol of the appropriate alcohol are in each case added to the residue. The mixture is then stirred at 50° C. for 1 h and worked up by vacuum distillation. The results are compiled in Table 1.

The $^1$H- and $^{29}$Si-NMR spectra corresponded to the assumed structure.

TABLE 1

Diacetoxydialkoxysilanes

| No. | Alcohol employed | Compound | Yield [%] | Boiling range [°C./mbar] |
|---|---|---|---|---|
| 1 | Ethanol | $(CH_3COO)_2Si(OCH_2CH_3)_2$ | 54 | 74–87/1.5<br>32–37/0.4–0.7 |
| 2 | Isopropanol | $(CH_3COO)_2Si[OCH(CH_3)_2]_2$ | 56 | 41–45/0.5–2 |
| 3 | n-Butanol | $(CH_3COO)_2Si[O(CH_2)_3CH_3]_2$ | 56 | ca. 68/1 |
| 4 | t-Butanol | $(CH_3COO)_2Si[OC(CH_3)_3]_2$ | 82 | 68–70/0.5 |

We claim:

1. A process for preparing a silane of the formula I $$R^1{}_n SiR^2{}_m \quad (I)$$

where $R^1$ is —O—Y, n is an integer from 1 to 3, $$-O-\overset{\overset{O}{\|}}{C}-Z,$$

m is an integer from 1 to 3 and n+m=4, and

Y and Z are each, independently of one another, unsubstituted or mono- or polyhalo-substituted $C_1$–$C_{20}$-alkyl, $C_2$–$C_{20}$-alkenyl, $C_2$–$C_{20}$-alkynyl and —$(CH_2)_p$—A, where p is an integer from 0 to 6 and A, which is unsubstituted or substituted by one or more $C_1$–$C_6$-alkyls, is a 3- to 20-membered hydrocarbon ring, which comprises reacting a halosilicon compound of the formula II $$SiX_4 \quad (II)$$

where

X is fluorine, chlorine, bromine and iodine, with compounds of the formula III and IV, or with an anhydride of the formula V and the compound of the formula IV $$MR^2 \quad (III)$$

$$H-R^1 \quad (IV)$$

$$Z-\overset{\overset{O}{\|}}{C}-O-\overset{\overset{O}{\|}}{C}-Z \quad (V)$$

where $R^1$ and $R^2$, and Z have the above meanings,

M is a metal of main group one and two.

2. Process as claimed in claim 1, where Y and Z are each, independently of one another, $C_1$—$C_{20}$-alkyl, $C_3$—$C_{20}$-cycloalkyl and $C_6$—$C_{14}$-aryl.

3. A process as claimed in claim 1, where Y is tert-butyl and Z is methyl.

4. A process as claimed in claim 1, wherein the reaction takes place as a one-pot process.

5. A process as claimed in claim 1, wherein the reaction takes place in an aprotic solvent.

6. A process as claimed in claim 1, wherein the reaction takes place at a temperature in the range from 10° to 100° C.

7. A process as claimed in claim 1, wherein M is a metal of main group I, preferably Na.

8. A process as claimed in claim 1, wherein the compound of the formula IV is used only after starting to use the compound of the formula III or V.

9. A process as claimed in claim 1, wherein silicon tetrachloride is reacted with sodium acetate and subsequently with tert-butanol to give diacetoxydi-tert-butoxysilane in hexane at 40° to 60° C.

10. A process as claimed in claim 1, wherein silicon tetrachloride is reacted with acetic anhydride and subsequently with tert-butanol to give diacetoxydi-tert-butoxysilane at 40° to 60° C.

11. A process for preparing a silane of the formula I $$R^1{}_n SiR^2{}_m \quad (I)$$

where $R^1$ is —O—Y, n is an integer from 1 to 3, $$-O-\overset{\overset{O}{\|}}{C}-Z,$$

m is an integer from 1 to 3 and n+m=4, and

Y and Z are each, independently of one another, unsubstituted or mono- or polyhalo-substituted $C_1$—$C_{20}$-alkyl, $C_2$—$C_{20}$-alkenyl, $C_2$—$C_{20}$-alkynyl and —$(CH_2)_p$—A, where p is an integer from 0 to 6 and A, which is unsubstituted or substituted by one or more $C_1$–$C_6$-alkyls, is a 3- to 20-membered hydrocarbon ring, which comprises reacting a halosilicon compound of the formula II $$SiX_4 \quad (II)$$

where

X is fluorine, chlorine, bromine and iodine, with compounds of the formula III and IV, or with an anhydride of the formula V and the compound of the formula IV $$MR^2 \quad (III)$$

$$H-R^1 \quad (IV)$$

$$Z-\overset{\overset{O}{\|}}{C}-O-\overset{\overset{O}{\|}}{C}-Z \quad (V)$$

where $R^1$ and $R^2$, and Z have the above meanings,

M is a metal of main group one and two, where Y is tert-butyl and Z is methyl.

12. A process as claimed in claim 11, wherein the reaction takes place as a one-pot process.

13. A process as claimed in claim 11, wherein the reaction takes place in an aprotic solvent.

14. A process as claimed in claim 11, wherein the reaction takes place at a temperature in the range from 10° to 100° C.

15. A process as claimed in claim 11, wherein M is a metal of main group I, preferably Na.

16. A process as claimed in claim 11, wherein the compound of the formula IV is used only after starting to use the compound of the formula III or V.

17. A process as claimed in claim 11, wherein silicon tetrachloride is reacted with sodium acetate and subsequently with tert-butanol to give diacetoxydi-tert-butoxysilane in hexane at 40° to 60° C.

18. A process as claimed in claim 11, wherein silicon tetrachloride is reacted with acetic anhydride and subsequently with tert-butanol to give diacetoxydi-tert-butoxysilane at 40° to 60° C.

19. A process for preparing a silane of the formula I $$R^1{}_n SiR^2{}_m \tag{I}$$

where $R^1$ is —O—Y, n is an integer from 1 to 3, $$-O-\underset{\underset{O}{\|}}{C}-Z,$$

m is an integer from 1 to 3 and n+m=4, and Y and Z are each, independently of one another, unsubstituted or mono- or polyhalo-substituted $C_1$—$C_{20}$-alkyl, $C_2$—$C_{20}$-alkenyl, $C_2$—$C_{20}$-alkynyl and —$(CH_2)_p$—A, where p is an integer from 0 to 6 and A, which is unsubstituted or substituted by one or more $C_1$–$C_6$-alkyls, is a 3- to 20-membered hydrocarbon ring, which comprises reacting a halosilicon compound of the formula II $$SiX_4 \tag{II}$$

where

X is fluorine, chlorine, bromine and iodine, with compounds of the formula III and IV, or with an anhydride of the formula V and the compound of the formula IV $$MR^2 \tag{III}$$

$$H-R^1 \tag{IV}$$

$$\underset{\underset{Z-C-O-C-Z}{}}{\overset{O\quad\;\; O}{\|\quad\;\;\|}} \tag{V}$$

where $R^1$ and $R^2$, and Z have the above meanings,

M is a metal of main group one and two, where

Y is tert-butyl and Z is methyl the wherein the reaction takes place as a one-pot process, wherein the reaction takes place at a temperature in the range from 10° to 100° C.

* * * * *

UNITED STATES PATENT AND TRADEMARK OFFICE
CERTIFICATE OF CORRECTION

PATENT NO. : 5,817,853
DATED : October 6, 1998
INVENTOR(S) : FRIEDRICH et al.

It is certified that error appears in the above-identified patent and that said Letters Patent is hereby corrected as shown below:

Col. 9, claim 1, line 25, before the formula insert --$R^2$ is--.

Col. 10, claim 11, line 35, before the formula insert --$R^2$ is--.

Col. 10, claim 11, line 39, "$C_1$-$C_{20}$-" should be --$C_1$-$C_{20}$- --.

Col. 11, claim 19, line 25, before the formula insert --$R^2$ is--.

Signed and Sealed this

Sixteenth Day of March, 1999

Attest:

Q. TODD DICKINSON

Attesting Officer

Acting Commissioner of Patents and Trademarks

US005817853C1

(12) EX PARTE REEXAMINATION CERTIFICATE (5038th)
United States Patent
Friedrich et al.

(10) Number: US 5,817,853 C1
(45) Certificate Issued: Dec. 14, 2004

(54) PREPARATION OF ACYLOXYALKOXYSILANES

(75) Inventors: Holger Friedrich, Bobenheim-Roxheim (DE); Bernd Leutner, Frankenthal (DE); Norbert Mronga, Dossenheim (DE); Raimund Schmid, Neustadt (DE)

(73) Assignee: BASF Aktiengesellschaft, Ludwigshafen (DE)

Reexamination Request:
No. 90/005,671, Mar. 7, 2000

Reexamination Certificate for:
Patent No.: 5,817,853
Issued: Oct. 6, 1998
Appl. No.: 08/909,941
Filed: Aug. 12, 1997

Certificate of Correction issued Mar. 16, 1999.

(30) Foreign Application Priority Data

Aug. 12, 1996 (DE) .......................................... 196 32 483

(51) Int. Cl.⁷ ............................... C07F 7/08; C07F 7/12
(52) U.S. Cl. ....................................................... 556/442
(58) Field of Search .......................................... 556/442

(56) References Cited

U.S. PATENT DOCUMENTS

| | | | |
|---|---|---|---|
| 3,296,161 A | 1/1967 | Kulpa | 260/18 |
| 3,296,195 A | 1/1967 | Goossens | 260/46 |
| 5,208,359 A | 5/1993 | Seiler et al. | 556/442 |
| 5,241,096 A | 8/1993 | Kinami et al. | 556/442 |
| 5,387,706 A | 2/1995 | Rasmussen et al. | 556/442 |

FOREIGN PATENT DOCUMENTS

EP          465723        1/1992

OTHER PUBLICATIONS

Sujecki et al., "On the reactions of Benzoyloxytrichlorosilane with Lower Fatty Acids", Annales Academial Medical Gedanesis, 3, 57–66, 1973, Poland.

Primary Examiner—Samuel Barts

(57) ABSTRACT

A process for preparing a silane of the formula I $$R^1{}_n SiR^2{}_m \qquad (I)$$

where $R^1$ is —O—Y, n is an integer from 1 to 3, $R^2$ is $$-O-\overset{\overset{\displaystyle O}{\|}}{C}-Z,$$

m is an integer from 1 to 3 and n+m=4, and Y and Z are each, independently of one another, unsubstituted or mono- or polyhalo-substituted $C_1$—$C_{20}$-alkyl, $C_2$—$C_{20}$-alkenyl, $C_2$—$C_{20}$-alkynyl and —$(CH_2)_p$—A, where p is an integer from 0 to 6 and A, which is unsubstituted or substituted by one or more $C_1$–$C_6$-alkyls, is a 3- to 20-membered hydrocarbon ring entails reacting a halosilicon compound of the formula II $$SiX_4 \qquad (II)$$

where

X is fluorine, chlorine, bromine and iodine, with compounds of the formula III and IV, or with an anhydride of the formula V and the compound of the formula IV $$MR^2 \qquad (III)$$

$$H-R^1 \qquad (IV)$$

$$\underset{Z-\overset{\overset{\displaystyle O}{\|}}{C}-O-\overset{\overset{\displaystyle O}{\|}}{C}-Z}{} \qquad (V)$$

where $R^1$ and $R^2$, and Z have the above meanings, M is a metal of main group one and two.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

* * * * *